United States Patent [19]
Talley et al.

[11] Patent Number: 5,744,367
[45] Date of Patent: Apr. 28, 1998

[54] MAGNETIC PARTICLE BASED ELECTROCHEMILUMINESCENT DETECTION APPARATUS AND METHOD

[75] Inventors: David B. Talley, Olney; Jonathan K. Leland, Silver Spring, both of Md.

[73] Assignee: IGEN International, Inc., Gaithersburg, Md.

[21] Appl. No.: 339,237

[22] Filed: Nov. 10, 1994

[51] Int. Cl.[6] .................................................. G01N 21/76
[52] U.S. Cl. ........................ 436/172; 250/361 C; 422/52
[58] Field of Search ........................... 250/361 C; 422/52; 436/172

[56] References Cited

U.S. PATENT DOCUMENTS

| | | | |
|---|---|---|---|
| 4,554,088 | 11/1985 | Whitehead et al. | 252/62.54 |
| 4,628,037 | 12/1986 | Chagnon et al. | 436/526 |
| 4,695,392 | 9/1987 | Whitehead et al. | 252/62.54 |
| 4,695,393 | 9/1987 | Whitehead et al. | 252/62.54 |
| 4,698,302 | 10/1987 | Whitehead et al. | 435/94 |
| 5,466,417 | 11/1995 | Ghaed et al. | 422/52 |

FOREIGN PATENT DOCUMENTS

| | | |
|---|---|---|
| 0 180 384 | 5/1986 | European Pat. Off. |
| 19501916 | 7/1995 | Germany. |
| 86/02734 | 5/1986 | WIPO. |
| 89/04302 | 5/1989 | WIPO. |
| 90/05301 | 5/1990 | WIPO. |
| 92/14138 | 8/1992 | WIPO. |
| 9214138 | 8/1992 | WIPO. |
| 9214139 | 8/1992 | WIPO. |
| 9301308 | 1/1993 | WIPO. |

OTHER PUBLICATIONS

Kenten et al., *Clinical Chemistry*, vol. 38, No. 6, Jun. 1992 pp. 873–879.
Blackburn et al., *Clinical Chemistry*, Electrochemiluminescence Detection for Immunoassays, vol. 37, No. 8, Sep. 1991, pp. 1534–1539.
Massay, Richard, *Biomedical Products*, "Electrochemiluminescence: A novel detection system . . . ", Oct., 1992.
Kenten, J.H. et al., 37, *Clin. Chem.*, pp. 1626–1632 (Jun. 1991).
Kenten, J.H. et al., 6, *Mol. Cell. Probes*, pp. 495–503 (1992).
DiCesare, J. et al., 15, *Biotechniques*, p. 152 (Jul. 1993).

*Primary Examiner*—Kathryn L. Gorgos
*Assistant Examiner*—John S. Starsiak, Jr.
*Attorney, Agent, or Firm*—Whitman Breed Abbott & Morgan LLP; Barry Evans, Esq.

[57] ABSTRACT

A method and apparatus for measuring electrochemiluminescence from a sample composition are described wherein magnetically responsive electrochemiluminescent active species are captured on the electrode with the aid of a capture magnet having a configuration such that the magnetic flux lines (or the magnetic field gradient) of at least one magnetic field source therein are compressed and/or dispersed. This capture magnet improves the distribution of the magnetically responsive electrochemiluminescent active species on the electrode surface and reduces interference with the photomultiplier tube, thereby enhancing the ECL signal and improving sensitivity. The improved capture and distribution also allows for shorter assay times.

23 Claims, 8 Drawing Sheets

MAGNETIC PARTICLE BASED ELECTROCHEMILUMINESCENT DETECTION APPARATUS AND METHOD

FIELD OF THE INVENTION

The present invention relates to an electrochemiluminescent detection apparatus and method for performing assays therewith wherein the sample compositions analyzed contain ECL-active species linked to magnetically responsive microparticles captured on the surface of the electrode, with the aid of one of more magnets, to initiate a chemiluminescent reaction.

BACKGROUND OF THE INVENTION

Electrochemiluminescence is the basis for highly sensitive detection and quantitation processes in which reactive species are electrochemically generated from stable precursors at the surface of an electrode. The electrochemically generated reactive species undergo a chemiluminescent reaction. The luminescence from the chemiluminescent reaction is used to detect or quantify ECL-active species. Highly sensitive electrochemiluminescence detection systems and methods have been developed which are capable of measuring trace amounts of materials. The detection of luminescence from ECL-active labels has been used to develop assays in materials such as biochemical and biological substances and provide sensitive immunoassays and DNA probe assays.

These electrochemiluminescent detection systems have many advantages over other detection systems in that measurement is simple and rapid, no radioisotopes are used, the detection limits for ECL-active species are extremely low (200 fmol/L); the dynamic range of the ECL-active specific quantification extends over six orders of magnitude; and the ECL-active labels are extremely stable and small (~1000 Da) so that haptens or large molecules can be labeled and multiple labels can be coupled to proteins or oligonucleotides without affecting their immunoreactivity, solubility or their ability to hybridize.

In addition, since the chemiluminescence requires an applied voltage, the initiation and duration of the response can be controlled by controlling the voltage applied to an electrode. ECL detection apparatus and methods are described in more detail in the following PCT published applications: US85/01253 (WO86/02734), US87/00987 (WO 87/06706), US88/03947 (WO89/04302).

A variety of formats have been developed for assays based on the detection and quantitation of electrochemiluminescence. For example, heterogenous (one or more separations) and homogeneous (non-separation) formats have been developed for competitive assays where haptens labeled with an ECL-active moiety compete for antibody with an analyte of interest. In heterogenous formats, the free and bound fractions of the labeled component such as hapten are separated before analysis in the ECL detection apparatus. If the efficiency of ECL excitation differs considerably for the free and bound fractions of the labeled components, ECL intensity from one fraction can be quantified in the presence of the other fraction in a homogeneous format.

PCT Published Application US89/04919 (WO90/05301) describes methods for performing assays based on luminescent phenomena in a homogeneous format wherein modulation of the intensity of the luminescent signal generated by the ECL-active moiety provides a means for monitoring the specific binding of an assay system. In these methods, microparticles are bound to ECL-active species of the assay components to modulate the intensity of the luminescent signal.

PCT Published Application US92/00982 (WO92/14138) describes methods for performing assays wherein the microparticles bound to the ECL-active species are magnetically responsive and are drawn to the electrode where the ECL-active moiety undergoes excitation by a plurality of north-south oriented magnets. This significantly enhances the ECL signal from the sample composition.

In the absence of a magnet, transport of the magnetically responsive microparticles to the electrode surface for the excitation is largely dictated by Brownian motion. With the incorporation of magnets to capture the magnetically responsive microparticles on the surface of the electrode, excitation of the bound fraction of the ECL-active species is more efficient; in fact, the signal from the bound fraction is greatly enhanced over that of the free fraction so that assays in a homogeneous format can be performed.

The inclusion of magnetically responsive microparticles has found particular advantage in methods for performing assays such as DNA probe assays where polymerase chain reaction (PCR) is employed to amplify the DNA present. In such assays, the PCR reaction is first performed to amplify the specific gene with two primers, one of which is biotinylated primer. The double stranded DNA formed with biotinylated primer is bound to streptovidin-coated microparticles and the DNA strands are separated. The particle bound strand is hybridized with a DNA probe having an ECL-active label which can be detected and quantified in an ECL-detection apparatus, typically one employing a magnet.

While the apparatus and methods taught in the prior art such as US89/04919 (WO90/05301) and US92/00982 (WO92/14138) and commercial apparatus such as the Origin® 1.5 analyzer by IGEN Inc. permit detection and quantitation of extremely small quantities of analytes in a variety of assays, there is a continuing effort to lower the detection limits and increase the sensitivity of assays performed and also to increase the speed at which assays are performed.

One means for lowering the detection limits and increasing sensitivity of assays is to increase the ECL signal from the sample composition. This can be accomplished by improving particle capture from the sample composition such as by employing a long residence time of the sample composition within the measurement cell to allow more particles to be captured on the electrode surface. Another means for improving sensitivity is to improve the distribution of particles on the electrode. Particles which have piled up on top of other particles are believed to position the ECL active species too far from the electrode surface to luminesce upon applying a voltage to the electrode. A more even distribution of particles on the electrode surface will allow more ECL active species to luminate, increasing the ECL signal. Conventional ECL detection devices which employ one or more standard magnets provide effective particle capture and particle distribution in a short period of time, but improvements are desired.

Particle capture is dependent on the magnetic force pulling the magnetically responsive particles to the electrode surface through the solution. This magnetic force is typically the product of the magnetic saturation of the particles and the magnetic field gradient. The magnetic pulling force can be increased with the selection of magnetic particles with a high magnetic saturation but once selected, the magnetic field gradient must be increased to increase this magnetic force.

Increasing the magnetic field strength of the magnet employed will increase the magnetic field gradient and improve particle capture. However, increasing the magnetic field strength can result in other problems such as increased interference with the photomultiplier tube. As the strength of the magnetic field increases, so does its size, typically extending further from the surface of the electrode and closer to the photomultiplier tube. This can result in a reduction in the ECL signal and lost sensitivity. In addition, increasing the magnetic field strength may lead to a piling up of particulates on the electrode, resulting in a reduction in the ECL signal.

OBJECTS OF THE INVENTION

It is a general object of this invention to provide an electrochemiluminescent detection apparatus with improved sensitivity and faster assay times.

It is another general object of the present invention to provide a method of measuring electrochemiluminescence within a sample composition with increased sensitivity and speed.

It is another object of the present invention to provide an ECL detection apparatus and method which employ a capture magnet of a configuration which provides for improved capture of magnetically responsive microparticles within sample compositions without increasing interference with the photomultiplier tube.

It is an additional object of the present invention to provide an ECL detection apparatus and method which employ a capture magnet of a configuration which provides for a more uniform distribution of particles on the electrode surface.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DESCRIPTION OF TERMS

The terms "ECL moiety", "ECL active moiety" and "label" are used interchangeably and refer to substituents such as $Ru(bpy)_3^{2+}$ which are linked to molecules such as an analyte, an analog of an analyte, a binding partner of an analyte or an analog thereof or other components of an assay which generate electrochemiluminescence upon exposure to an applied voltage.

The terms "electrochemiluminescence", "electrochemiluminescent", "luminescence", "luminescent" and "luminesce" include the emission of light and other forms of electromagnetic radiation. The terms "detection" and "quantitation" are referred to as "measurement". It being understood, a quantitation may require preparation of reference compositions and calibrations. The terms "magnetic flux lines", "lines of induction", "magnetic flux", "flux lines," and "magnetic field lines" are used interchangeably and refer to those lines which define a magnetic field by the force which would be applied on a magnetically responsive object at that location. Compression and/or dispersion of the magnetic flux lines will result in compression and/or dispersion of the magnetic field gradient and may also result in compression and/or some expansion in size and shape of the magnetic field.

The term "magnetic field source" includes permanent magnets and electromagnets, which are separate, individual entities with defined N-S magnetic poles. The term "magnetic field source" also includes regions within a composite material or structure which generate a magnetic field. Such regions can be produced within a composite from magnetic iron oxide particulates.

SUMMARY OF THE INVENTION

The above objectives and others have been accomplished by employing a capture magnet within an ECL detection apparatus having a configuration wherein the magnetic flux lines of the magnetic field source(s) employed therein are redirected by compression and/or dispersion.

Where the magnetic flux lines are dispersed only, dispersion is accomplished without increasing the magnetic field strength, i.e., without adding another magnetic field source to the configuration. When dispersing the magnetic flux lines in this manner, the distribution of the magnetic field gradient can be altered and enhanced without increasing the strength of the magnetic field. Therefore, the magnetic field gradient can be manipulated to spread across the electrode surface without significant extension of the magnetic field from the surface.

Where the magnetic flux lines are compressed, the magnetic flux density (magnetic field strength) of the magnetic field is increased without significantly extending the magnetic field from the surface of the electrode.

Both configurations serve to enhance bead capture efficiency on the electrode by spreading the magnetic field gradient on the surface and lessening interference with the photomultiplier tube.

An embodiment of this invention is an apparatus for the measurement of electrochemiluminescence from a sample composition which comprises:

a) a cell having a volume which defines the sample composition, an electrode adapted to apply a voltage to the sample composition and a magnet adapted to attract magnetically responsive components within the sample composition to the electrode surface;

b) means to impress a voltage upon said electrode sufficient to generate luminescence from electrochemiluminescent (ECL) active species within the sample composition; and c) means to measure the luminescence generated by the ECL-active species within the sample composition, wherein the magnet is positioned below said electrode and has a configuration such that the magnetic flux lines of at least one magnetic field source within the magnet is compressed and/or dispersed, subject to the proviso that where the magnetic flux lines are dispersed only, the magnet contains only one magnetic field source.

The invention also provides a method for measuring electrochemiluminescence from a sample composition, wherein said sample composition contains an electrochemiluminescent (ECL) active species that comprises an ECL-active moiety and a magnetically responsive particle, said method comprising:

a) introducing a known volume of said sample composition into a measurement cell which contains an electrode;

b) collecting the ECL-active species that comprises an ECL-active moiety and a magnetically responsive particle on a surface of said electrode by imposition of a magnetic field on said magnetically responsive particles;

c) imposing a voltage on said electrode of sufficient magnitude to induce luminescence from the ECL-active species within the sample composition; and d) measuring the luminescence emitted from the sample composition, wherein the magnetic field imposed on said magnetically responsive particles is provided by a capture magnet positioned below the electrode surface comprising one or more magnetic field sources, said capture magnet having a configuration such that the magnetic flux lines of at least one magnetic field source within the capture magnet are compressed and/or dispersed, subject to the proviso that where the magnetic flux lines are dispersed only, the magnet contains only one magnetic field source.

Several different heterogeneous and homogeneous formats to collect and concentrate the complex on the surface of an electrode can be employed in performing the method described above. In a heterogeneous assay, the bound fraction is concentrated on the surface of the working electrode and the ECL signal is measured in the presence of the unbound fraction in the measurement cell. In a modified heterogeneous format, an in situ separation step is performed after the sample composition has been pumped into the measurement cell and the bound fraction is captured on the working electrode. In this in situ separation step, a second fluid is pumped through the cell to separate the unbound fraction from the bound fraction of the ECL-active species. The ability to perform the separation of the bound and unbound fractions inside the measurement cell is advantageous in that it does not require additional separation apparatus and the procedure is generally much faster than external separation methods. Measuring the ECL signal from the bound fraction after such a separation step provides greater accuracy and lower detection limits than is possible without separation.

DETAILED DESCRIPTION OF THE PREFERRED EMBODIMENTS

Figure 1:
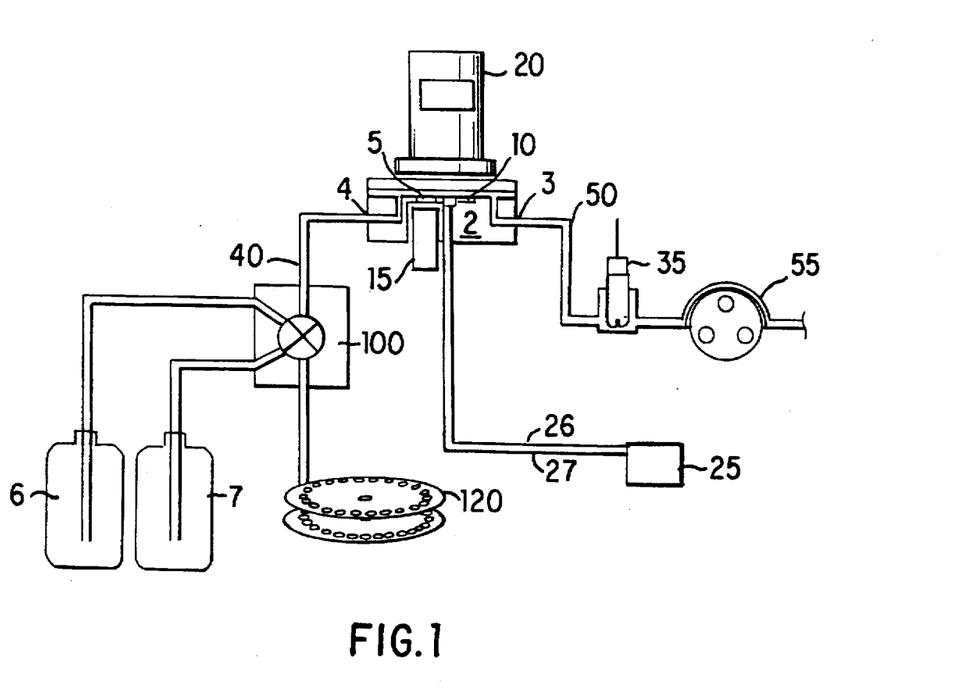
FIG. 1 is a schematic representation of the basic configuration of an ECL detection system of the present invention.

FIG. 1 illustrates the primary components of an ECL detection system within the scope of this invention. The heart of the instrument is the cell 2, an electrochemical flow cell as shown, containing a working electrode 5, a counter electrode 10 and a magnet 15.

Figure 2:
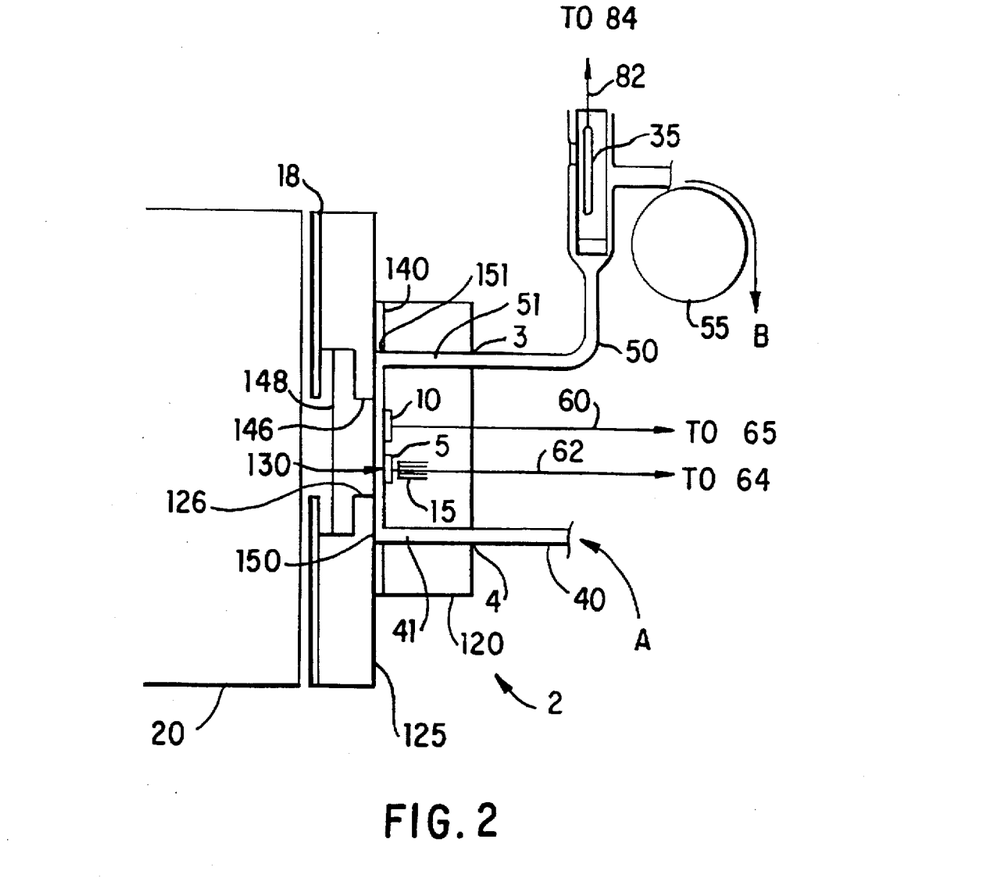
FIG. 2 is a schematic representation of a flow cell of an ECL detection apparatus of the present invention and the components of the ECL detection apparatus which interact with the flow cell.

FIG. 2 provides a more detailed illustration of an electrochemical flow cell that can be used in the apparatus of the present invention.

Working electrode 5 and counter electrode 10 initiate the ECL reaction when a voltage is applied thereto by a voltage source 25 via leads 26 and 27. Preferably, these electrodes are fabricated from gold but other materials have been used with various degrees of success. A light detection means 20 detects the light emitted during the ECL reaction and may advantageously be a photomultiplier tube (PMT), photodiode, charge coupled device photographic film or emulsion or the like. A reference electrode 35 is placed in a fluid path 50 downstream from flow cell 2. A pump 55 draws various fluids through flow cell 2 via fluid path 50. Fluid path 50 can be a simple conduit which leads from an outlet 3 of flow cell 2. Sample compositions are introduced to the flow cell by a fluid path 40 through an inlet 4. Fluid path 40 can be a simple conduit which feeds fluids from a fluid control means 100. Fluid control means 100 controls the fluid which enters flow cell 2 from various sources. In FIG. 1, bulk sources 6 and 7 are shown, which can be bulk sources of cleaning solution and/or conditioning solution for flow cell 2, and also a sample source 120 for sample compositions, which can be a test tube array. Voltage source 25 is typically a potentiostat that can apply various voltage wave forms through the electrodes via leads 26 and 27.

This invention can employ fluid handling components, luminometers and potentiostats found in the commercially available ECL detection systems, such as the components employed in the Origen® 1.5 analyzer by IGEN, Inc., Rockville, Md.

In a typical sequence, a sample composition is drawn from the sample source 120, typically within a test tube, and into flow cell 2 via a vacuum provided by pump 55. The magnetically responsive particles within the sample composition are captured on electrode 5 by a magnetic field from magnet 15. Optionally, the particles are washed to remove ECL active compounds which are not bound to the magnetically responsive particles. These include free or unbound ECL active compounds and ECL active components which are engaged in non-specific binding, i.e., the particles are not bound to the ECL active moiety at the specific site of interest.

A ramp voltage is applied to working electrode 5 and counter electrode 10 via potentiostat 25 and emitted light is measured with photomultiplier tube 20. Following measurement, cleaning solution and/or conditioning solution may be drawn into cell 2 from source 6 and/or 7 via controller 100, if desired. A voltage wave form is typically applied when the conditioning solution is within the cell to "condition" or standardize the surface of the electrode to provide reproducible measurements. In preferred embodiments, the manipulation of the fluid handling components for the samples, cleaning solution and/or conditioning solution is automated.

FIG. 2 shows a more detailed illustration of the cell 2 and reference electrode 35. The apparatus shown in FIGS. 1 and 2 incorporate a flowthrough cell. However, one skilled in the art will recognize that a static cell can be easily incorporated in these detection systems and that the present invention encompasses such apparatus, although they are not preferred. The light detection means 20 can be any of the embodiments described above for the apparatus in FIG. 1, but is preferably a photomultiplier tube (PMT). The apparatus includes a pump 55, which is also advantageously a peristaltic pump which provides means for fluid transport to, through and from the cell 2. A positive displacement pump can also be used. A shutter mechanism 18 is provided between cell 2 and PMT 20 and is optional. Preferably, the shutter 18 is controllably operated to open only so far as to expose PMT 20 to cell 2 during ECL measurement. The shutter mechanism may be closed, for example, during maintenance. Cell 2 comprises mounting blocks 120 and 125, an annular spacer 140, and a window 148. A sample holding volume 130 is defined by mounting block 120 and 125, annular spacer 140 and window 148. Mounting blocks 120 and 125 are advantageously constructed of stainless steel, annular ring 140 is advantageously constructed of Teflon® and window 148 is advantageously formed with a material which is substantially transparent at the wavelength of electrochemical luminescent light emitted by the ECL active species in the cell such as glass, plastic, quartz or similar material. Mounting block 125 has a central aperture 126 in which window 148 is seal fitted. Mounting block 120 is connected to an inlet tube 40 at an inlet 4 and outlet tube 50 to an outlet 3 which are both preferably constructed of stainless steel. Inlet tube 40 feeds an inlet channel 41 and outlet tube 50 receives from outlet channel 51 within mounting block 120. Inlet channel 41 and outlet channel 51 open into sample holding volume 130. Inlet channel 41 intersects sample holding volume 130 at a first end 150 thereof adjacent to the spacer 140 and outlet channel 51 intersects sample holding volume 130 at a second end 151 thereof, adjacent spacer 140. The combination of inlet tube 40, inlet channel 41, sample holding volume 130, outlet channel 51, and outlet tube 50, thereby provides a continuous flow path for the narrow, substantially laminar flow of the sample composition to, through and from cell 2. Arrows A and B represent the flow into and out of inlet tube 40 and outlet tube 50, respectively.

Pump 55 is advantageously positioned at outlet tube 50 to pull solution from a sample volume in the direction of arrow A into inlet tube 40. The solution will flow through inlet tube 40, sample holding volume 130 and outlet tube 50 past reference electrode 35 and out in the direction of arrow B. Alternatively, pump 55 may be positioned at inlet tube 40 to push the solution through inlet tube 40, sample volume 130 and outlet tube 50. Pump 55 may be controlled to suspend its operation to hold a particular solution in cell 2 for a period of time. Advantageously, the same flow path through the inlet tube, sample holding volume and outlet tube is used for all solutions and fluids which pass through cell 2, thereby a fluid performs a hydrodynamic cleaning action, forcing the previous fluid out of cell 2. The flow through construction permits the rapid alternation between initialling steps and allows the working electrodes to be impressed with a variable voltage or continuously held at a preoperative potential while continuously exposed to one or more solutions without exposing these electrodes to air, which can cause random voltage fluctuations.

Mounted within sample holding volume 130 is a working electrode 5 and counter electrode 10. In other embodiments, multiple working electrodes may be utilized. These electrodes may be advantageously constructed of platinum, gold, carbon or other materials which are effective for this purpose.

Working electrode 5 and counter electrode 10 provide the interface to impress the potential on the solution within the sample holding volume 130 which energizes the chemical reactions and triggers electrochemiluminescence in this sample and/or provides energy for cleaning and conditioning the surfaces of the cell 2. Working electrode 5 is where the electrochemical and ECL reactions of interest take place.

Reference electrode 35 provides a reference voltage to which the voltage applied by the working electrode 5 is referred, for example, +1.2 volts versus the reference, and is advantageously located in outlet tube 50 at a position remote from cell 2. Wire leads 60, 62 and 82 connect working electrode 5, counter electrode 10 and reference electrode 35, respectively, to a voltage control source, which is not shown. Suitable voltage control sources include the conventional potentiostats and operating circuits described in Published PCT Appln. US92/00982 (WO92/14138).

Figure 3:
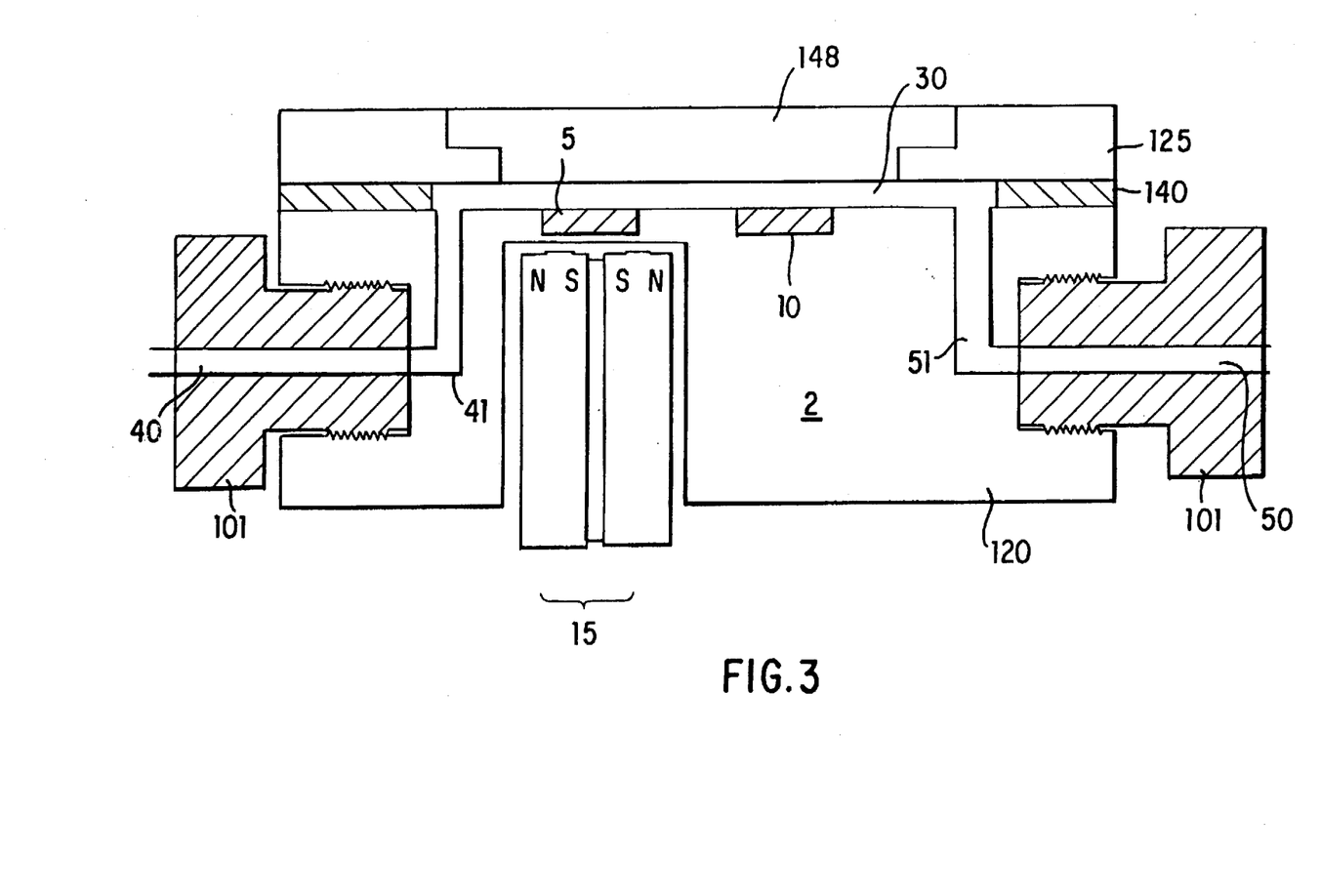
FIG. 3 is a schematic representation of a flow cell of an ECL detection apparatus of this invention with a capture magnet having a sandwich configuration.

FIG. 3 is another illustration of the electrochemical cell 2 employed in the apparatus of the present invention. Relative positioning is shown with respect to the working electrode 5, counter electrode 10, magnet 15, sample volume 130 and lens 148. Connectors 101 provide means for connecting inlet tube 40 to inlet channel 41, and outlet tube 50 to inlet channel 51 of base 120. Magnet 15 illustrated in FIG. 3 has a sandwich configuration consistent with the present invention, discussed more particularly below.

The magnets employed in the apparatus and methods of this invention have a configuration wherein the magnetic flux lines of the magnetic field source(s) are dispersed and/or compressed, i.e., the magnetic field gradient is dispersed or compressed. By manipulating the magnetic flux lines in this manner, the shape and density of the magnetic field can be controlled without expanding significantly in size. The shape and distribution of the magnetic field can be controlled to provide for a more even distribution over the electrode surface without significant extension from the electrode surface, which translates to a more even distribution of particles captured on the electrode (less piling up) with no significant increase in PMT interference.

Figure 4:
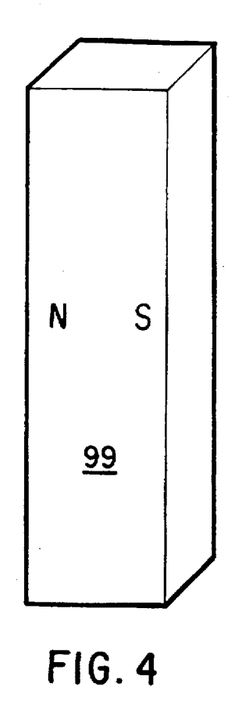
FIG. 4 is a perspective representation of the standard magnet employed in conventional ECL detection devices as a capture magnet.
Figure 5:
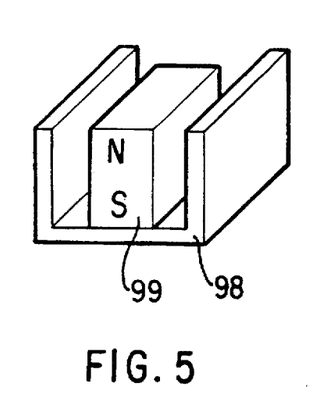
FIG. 5 is a perspective representation of a channel magnet used in ECL detection devices of the present invention as a capture magnet.
Figure 9:
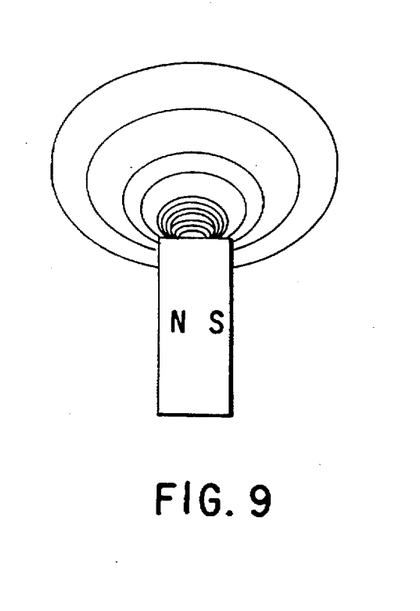
FIG. 9 is a representation of the magnetic field lines of a standard magnet as in FIG. 4.

FIG. 4 illustrates a standard magnet known in the art which comprises a single magnetic field source 99, i.e., one N-S pole pair, and FIG. 9 is a representation of its magnetic field. FIG. 5 illustrates a magnet suitable for use in this invention referred to herein as a "channel" magnet wherein a single magnetic field source 99 is bonded to a highly magnetizable material 98 in the form of a U-shaped channel. In such a configuration, magnetizable material 98 becomes an extension of the magnetic pole to which it is bound. With the extension of the magnetic pole (S) to both sides of the opposite pole (N) of the pair, the magnetic flux lines from magnetic field source 99 are dispersed or extended over a larger surface area because one pole of the magnetic field source is essentially split. Magnet configurations wherein a magnet pole is extended to disperse the magnetic field can vary widely and such configurations will be apparent to one skilled in the art based on the disclosure herein. An important feature of this magnet configuration and others which provide dispersion only is that the magnetic lines of the flux are redirected without increasing the strength of the magnetic field by the application of a second magnetic field source.

Figure 8:
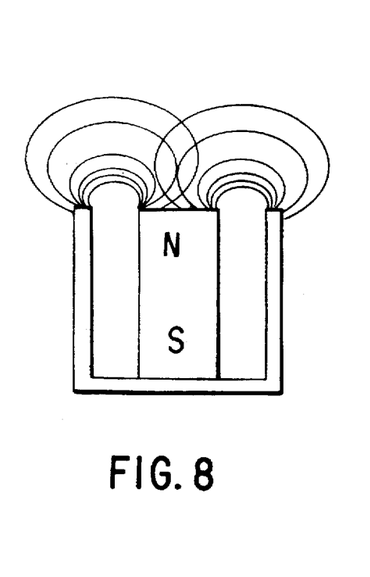
FIG. 8 is a representation of the magnetic field lines of a channel magnet as in FIG. 5.

FIG. 8 shows the magnetic flux lines that define the magnetic field for the channel magnet of FIG. 5. A similar pattern of flux lines could be achieved with three separate magnetic field sources. The magnetic field will be distributed over the same surface area but the magnetic flux lines will typically extend further from the electrode surface, causing interference with the photomultiplier tube due to the additive effect of three separate magnetic field sources. Employing a magnetically sensitive material to extend the magnetic pole allows for dispersion of the magnetic fields without increasing the magnetic field as a whole.

Magnetically sensitive materials which can extend a magnetic pole can vary widely in shape, size and composition. Essentially, any ferromagnetic material or alloy with a high magnetic saturation can be used. A material used with particular advantage is that referred to as Vanadium Permandur, which typically comprises 50% iron, 40% cobalt and 2% vanadium and is available from many sources including Applied Magnetics, Baltimore, Md. The use of a separate magnetically sensitive material to extend a magnetic pole allows magnets with complex configurations to be obtained. One component, single field source magnets with a similar configuration can be obtained but complex manufacturing methods are required.

Figure 6:
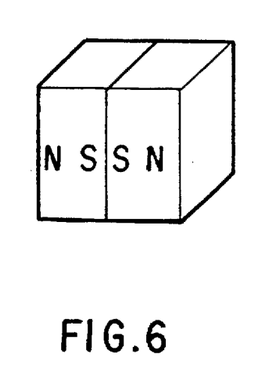
FIG. 6 is a perspective representation of a sandwich magnet used in the ECL detection devices of the present invention as a capture magnet.
Figure 7:
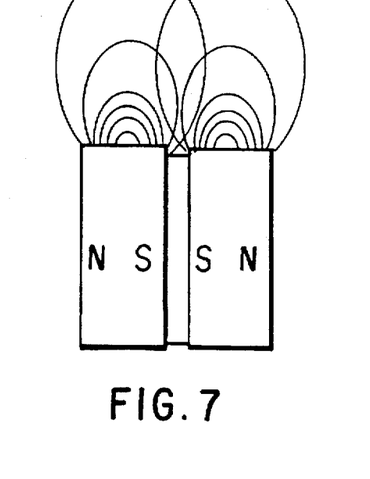
FIG. 7 is a representation of the magnetic field lines of a sandwich magnet as in FIG. 6.

In another embodiment of this invention, the magnet utilized to capture magnetic particles within the sample composition has a configuration wherein the magnetic flux lines are compressed, i.e., the magnetic field gradient is compressed. In such embodiments, two or more magnetic field sources are employed and configured such that their opposing magnetic fields overlap or are coerced. This is accomplished by placing opposing poles (N-N or S-S) in closer proximity to each other than the attracting poles (N-S) of the magnetic field sources, i.e., a "coercive" configuration. This includes adjoining opposing poles. FIG. 6 illustrates an example of a coercive configuration, referred to herein as a "sandwich magnet," wherein opposing poles are adjoined. FIG. 7 is a representation of the magnetic flux lines for such a magnet. In configuring two or more magnetic field sources in such a manner, the magnetic field as a whole is wider relative to that of a single magnetic field source and because the magnetic field gradient is compressed, the flux density is increased without significantly extending the magnetic field above the electrode surface as is the case wherein two or more magnetic field sources are configured with an additive configuration.

While FIG. 6 illustrates a sandwich magnet having two magnetic field sources, the present invention includes configurations having more than two magnetic field sources including four, five, six seven, eight, etc. However, employing only two magnetic field sources in the sandwich magnet simplifies construction and may be preferred in some ECL detection devices for this reason. The magnetic field sources employed may be permanent magnets or electromagnets but are preferably permanent magnets for simplicity of the construction of the cell. To form a sandwich magnet, standard permanent magnets can be simply bonded together by a conventional means such as with an epoxy or a high bond strength anaerobic adhesive.

Sandwich magnets, as in FIG. 6, provide a 30 or 40% increase in the capture signal over standard magnets as in FIG. 4 for the following magnetically responsive particles: Dynal 280 beads, Dynal 450 beads and Rhone-Poulenc beads. With the reduction in PMT interference, the increase in the ECL signal is even greater and is typically about 2.5 times greater with Dynal 280 beads, about 3.5 times greater with Dynal 450 beads, and 3.0 times greater with Rhone Poulenc beads under conventional operating conditions. Improved capture signals correlate to improved sensitivity. In addition to improving the capture signal through more effective particle capture, the sandwich magnets retain the particles more effectively as compared to standard magnets. Where the ECL detection apparatus has a flow through cell with sample compositions and washing solutions passing therethrough, the pump speed can be increased without a signal loss, allowing the cycle time to be shortened so that more samples can be analyzed per unit time. Similar improvements in capture signal and retention over standard magnets can be obtained with other magnet configurations where the magnetic field lines are compressed.

The magnet employed can vary significantly in shape and, to some extent, size. The size of the magnet is typically limited by the space available within the cell of the ECL detection apparatus. Rectangular shaped magnets having north-south poles extending along their longest dimension have found advantage in coercive configurations, allowing multiple opposing poles to be configured within a small volume. In preferred embodiments, a magnetically responsive substance is positioned between the magnetic field sources. This magnetically responsive substance redirects the magnetic flux lines to some extent in addition to spacing the magnetic field sources and serves to shape the magnetic field. In preferred embodiments, the magnetically responsive substance is, an alloy of iron or iron oxide such as Vanadium Permandur.

It is desirable to provide magnetic lines of force in the region above the working electrode which are nearly horizontal to the plane of the electrode. This induces an orientation of the magnetically responsive particles wherein the particles lie upon the surface of the electrode and the ECL-active moieties are readily assessable to the electrochemical energy supplied by the electrode. The apparatus shown in FIG. 3 shows the magnet positioned just below the electrode. However, in selected embodiments, a magnet may be movable relative to the electrode surface so as to allow for easy release or elimination of magnetically responsive particles at the electrode surface. For some embodiments, it has been found advantageous for the magnet to be pivotally anchored beneath the electrode so as to permit extension into the flow path to capture particles and retract from the flow path for ECL measurement. An arc of about 60° for the up position to the down position is typical. Such a configuration enhances capture efficiency without increasing interference with the PMT.

Although any type of permanent magnet can be used, neodymium-iron-boron alloys have been used with advantage in the sandwich magnet design and channel magnet design with Vanadium Permandur as the magnetically sensitive material which helps define the magnetic field shape and density. The magnets employed typically have a thin nickel coating to prevent corrosion. It has been found that magnet thicknesses of 20–30 mils are advantageous in sandwich magnets with Vanadium Permandur spacers of a similar thickness. The spacers can range in thickness from essentially zero, i.e., less than 0.01 times the magnet thickness to 2.0 times the thickness of the magnets employed.

The magnetic flux lines of capture magnets which extend from the electrode surface can presumably cause PMT interference by deflecting electrons from their normal trajectory when traveling from the photocathode to the first diode stage. The deflected electrons can result in lowered gain. When using the sandwich magnet, this effect is lessened considerably since its magnetic flux lines do not extend far from the surface of the electrode.

The use of magnets with the special configurations required of this invention shows particular advantage in ECL detection apparatus with flow through cells having a cell gap (the distance between the magnet top surface and the work- ing electrode surface) of less than 15 mils. The cell gap influences the performance of the magnet in capturing particles. Typical cell gaps range from 10–25 mils.

Methods of the present invention employ a magnet having a configuration which provides dispersed and/or compressed magnetic flux lines subject to the proviso that where the magnetic flux lines are dispersed only, the magnet contains only one magnetic field source. The method involves introducing a sample composition into a sample cell, wherein said sample composition contains magnetically responsive suspended particles with an ECL-active moiety bound thereto; imposing a magnetic field on the sample composition of sufficient strength to collect magnetically responsive particles at the surface of an electrode; imposing a voltage on said electrode sufficient to induce the ECL-active compound to luminesce and measuring the emitted luminescence. This method can be advantageously performed with the apparatus of the present invention such as that shown in FIG. 1, wherein a sample is drawn from carousel 120 via sample control means 100 and introduced to the cell 2. The magnetically responsive particles are collected on the surface of working electrode 5 with magnet 15. If pivotally anchored, magnet 15 is preferably in the up position and following the collection of magnetically responsive particles, the magnetic 15 is retracted from the up position. Optionally, the pump is turned off once particles are collected on the electrode surface and the sample composition is in the static state while a voltage is applied to electrode 5 and counter electrode 10 sufficient to induce luminescence. A photomultiplier tube then measures the luminescence emitted from the sample composition. After measurement, the sample cell may be purged of sample composition with a cleaning solution. Where pivotally anchored, the magnet can be retracted from the surface of the electrode to release the magnetically responsive particles. Following the release, a conditioning solution may be introduced to the sample cell and a voltage applied to condition the electrode surface for the next measurement.

The apparatus and method of the present invention are not limited to particular sample compositions. The samples may be solid, emulsions, suspensions, liquids or gases and may be derived from various sources such as cells, water, organic solvents, air and the like, such as those described in US 92/00982 (WO92/14138). The sample composition may contain an analyte of interest which can vary widely from cells, subcellular particles, viruses, haptens, antigens, antibodies, nucleic acids, proteins, and the like, such as those described more particularly in US92/00982 (WO 92/14138). Typically, the analyte of interest is present at low concentrations of less than about $10^{-3}$ molar and can be as low as $10^{-12}$ molar or lower. In some embodiments, the analytes of interest are capable of entering into a binding reaction such as a DNA or RNA interaction, an antigen-antibody reaction, a ligand receptor reaction and the like. This binding reaction may allow for the incorporation of a label, such as an ECL-active label. The labels may be incorporated on the analyte directly, on a binding partner, or through another reacting component. An alternative to labeling the analyte of interest directly or indirectly is to label an analog thereof which competes with the analyte. The use of binding partners and analogs of the analyte of interest is described more particularly in WO92/14138 where they are referred to as "assay-performance-substances".

Advantageously, the ECL-active moieties used as labels are metal chelates. Essentially any metal chelate which will luminescence under electrochemical conditions can be used as an ECL-active moiety. The metal can be, for example, a transition metal, such as a d-block transition metal, or a rare earth metal. Suitable transition metals include those selected from groups consisting of luthenium, osmium, ruthenium, iridium, rhodium, platinum, indium, palladium, molybdenum, technetium, copper, chromium, or tungsten. Preferred transition metals are ruthenium and osmium. The ligands which are linked to the metal of such metal chelates are usually heterocyclic or organic in nature and play a role in determining solubility. Examples of suitable ligands are the polydentate ligands and monodentate ligands described in WO92/14138. Examples of suitable metal chelates are as follows: bis[(4,4'-carbomethoxy)-2,2'-bipyridine]2-[3-(4-methyl-2,2'-bipyridine-4-yl)propyl]-1,3-dioxolane ruthenium (II); bis (2,2'-bipyridine) [4-(butan-1-al)-4'-methyl-2, 2'-bipyridine] ruthenium (II); bis(2,2'-bipyridine)[4-(4'-methyl-2,2'-bipyridine-4'-yl)-butyric acid] ruthenium (II); tris (2,2'bipyridine) ruthenium (II); (2,2'-bipyridine) [bis-bis (1,2-diphenylphosphino)ethylene] 2-[3-(4-methyl-2,2'-bipyridine-4'-yl)propyl]-1,3-dioxolaneosmium (II); bis(2,2'-bipyridine)[4-(4'-methyl-2,2'-bipyridine)-butylamine] ruthenium (II); bis(2,2'-bipyridine) [1-bromo-4(4'-methyl-2, 2'-bipyridine-4-yl)butane] ruthenium (II); bis (2,2'-bipyridine)maleimidohexanoicacid,4-methyl-2,2'-bipyridine-4'-butylamide ruthenium (II). Other suitable ECL active moieties are described in US92/00982 (WO92/ 14138), US88/03947 (WO89/04302) and US87/00987 (WO89/09379).

Preferred ECL-active moieties are those with tris(2,2'-bipyridine) ruthenium (II) which can undergo an electrochemiluminescent reaction with tripropylamine (TPA). The salts of ruthenium (II) tris(bipyridyl) are very stable, water soluble compounds which be chemically modified with reactive groups to form active moieties such as the Ru(bpy)$_3^{2+}$ NHS ester of formula I below.

These moieties can be bound to proteins, haptens, nucleic acids, etc.

Figure 12:
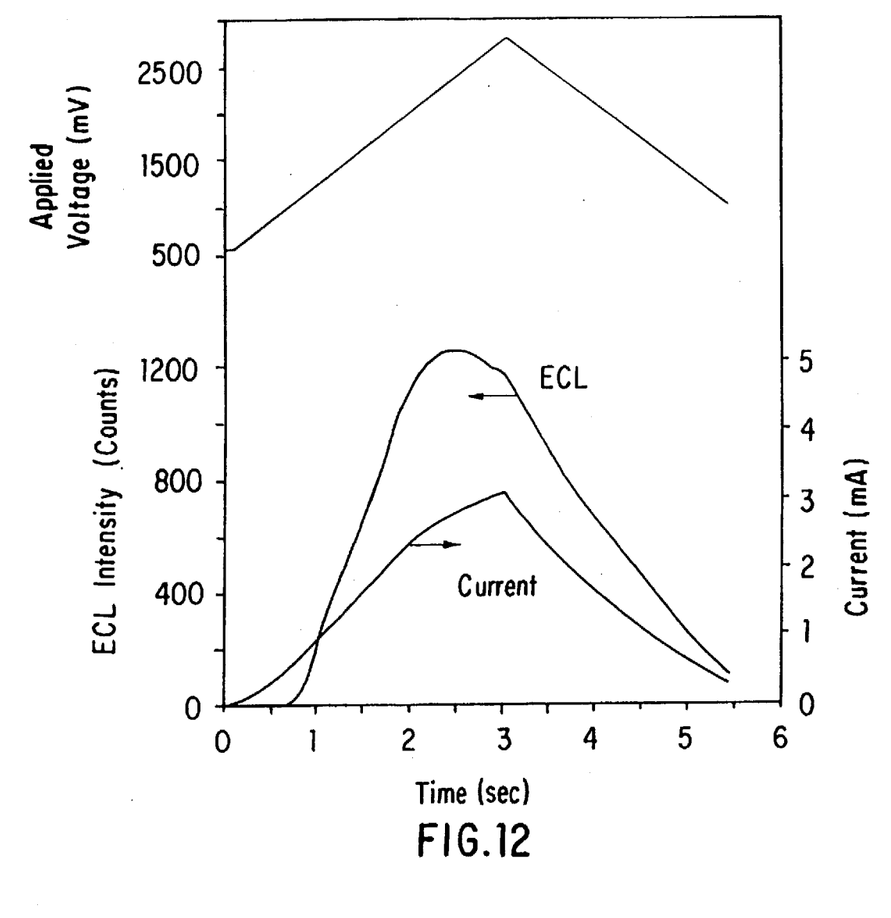
FIG. 12 is a graphic representation of the ECL signal measured by an ECL detection apparatus as a function of applied voltage.

The ECL reaction of the ECL-active species within the sample composition is initiated by an applied voltage. Many different voltage wave forms can be applied to initiate the ECL reaction. FIG. 12 illustrates measurements of the working electrode current and ECL intensity induced by the application of a triangle wave to the electrodes of an Origen® 1.5 analyzer with $Ru(bpy)_3^{2+}$ NHS ester of formula I above with TPA. The applied voltage as shown is actually the voltage measured at the reference electrode and includes the effects of a significantly uncompensated resistance; consequently, the actual voltage applied at the working electrode is substantially less than that depicted. The current that flows in the cell prior to applying a voltage to the electrodes is primarily the result of the oxidation of the TPA and of the hydrolysis of water. The electrochemiluminescent reaction becomes evident when the applied voltage reaches approximately 1100 mAs. The intensity of the luminescence is shown to increase with the applied voltage until the TPA at the surface of the electrode is depleted. The observed luminescence illustrated in FIG. 12 can be easily measured with conventional photomultiplier tubes.

As can be appreciated by one of ordinary skill in the art, the amount of metal chelate or other metal containing ECL moiety incorporated in the sample composition can vary widely from system to system. Generally, the amount of moiety utilized is that which is effective to result in the emission of a detectable and, if desired, quantitatable emission of electromagnetic energy from the sample composition. The detection and/or quantitation of an analyte of interest is typically made and compared to luminescence from the sample containing a known amount of analyte of interest as a calibration standard.

The particles to which the ECL moiety is bound advantageously comprise microparticulate matter having a diameter of 0.0001 to 200 µm. These microparticles must be magnetically responsive to and typically comprise iron dioxide, or other oxides of iron. The surface of the microparticles must contain a component capable of binding to the analyte of interest an analog thereof or a binding partner. Suitable examples are described in WO92/14138. These include cross-linked starch, dextrans, proteins, and the like. The density of the particles can vary widely and may typically have a density of from 1.0 to 5.0 g/ml and preferably have a density of from 1.1 to 2 g/ml. The concentration of the particles used in preparing the sample composition also vary widely such as, for example, 1–10,000 mg/ml, preferably 5–1000 mg/ml. Suitable magnetic particles are described in U.S. Pat. Nos. 4,628,037; 4,695,392; 4,695,393; 4,698,302; 4,554,088; and EP 0 180 384. The particles may be paramagnetic or ferromagnetic. It is desirable that the magnetic particles have a low magnetic resonance so that when the magnetic field is removed from the electrode surface, the particles demagnetize and are swept from the cell.

In order to introduce electrochemical energy to the ECL-active species in the sample composition, the electrode must be immersed in an electrolyte which typically is a solution of one or more salts or other species in water, an organic liquid or mixture thereof. Suitable examples are given in WO92/14138.

A variety of assays can be performed using the methods of this invention. The methods of this invention and apparatus of this invention are capable of measuring trace amounts of microorganisms, pharmaceuticals, hormones, viruses, antibodies, nucleic acids and other proteins.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, cited above and below, are hereby incorporated by reference.

EXAMPLES

Instrumentation

An ECL-detection apparatus as shown in FIGS. 1–3 having a capture magnet of a sandwich configuration of FIG. 6 is employed in the examples illustrating the invention. The sandwich magnet is substituted with a standard magnet of FIG. 4 in the comparative examples. The fluid handling components, luminometer, potentiostat and electrochemical flow cell of each apparatus are those of an Origen 1.5 analyzer with the following features, unless indicated otherwise:

Working electrode—Au disk, 3 mm diameter
Counter electrode—Au disk, 3 mm diameter
Reference electrode—Ag/AgCl
cell gap—12 mils.

Components of Sample Composition

ECL moiety—$Ru(bpy)_3^{2+}$-NHS ester=$Ru(2,2'$-bipyridyl$)_2$ (4-[3-(1,3-dioxylan-2-yl)propyl]-4'-methyl-2,2'-bipyridine$)^{2+}$ obtained from Igen, Inc.

ECL buffer—112 mM $KH_2PO_4$, 88 mM $K_2HPO_4.3H_2O$, 50 μm NaCl, 6.5 mM $NaN_3$, 0.8 μm Triton X-100, 0.4 mM Tween 20, 100 mM tripropylamine $H_2O$.

ECL diluent—37.5 mml $KH_2PO_4$, 109.2 mM $K_2HPO_4.3H_2O$, 151.7 mM NaCl, 0.65 mM $NaN_3$, 0.43 mM bovine serum albumin in $H_2O$.

Microparticles a) Dynal M-450 Dynabead, 4.5 μM diameter superparamagnetic particles, 30 mg/mL obtained from Dynal, 45 North Station Plaza, Great Neck, N.Y. 11021.

b) Dynal M-280 Dynabeads, 2.8 μM diameter superparamagnetic particles, 10 mg/mL, obtained from Dynal, 45 North Station Plaza, Great Neck, N.Y. 11021.

Coated Microparticles

The microparticles (Dynal beads M-280) are coated with protein by mixing 1 mL (30 mg) of particles in 150 micro moles/liter sodium carbonate bicarbonate buffer (pH 9.6) with an equal volume of 0.5 to 1.0 g/L of protein solution. This protein solution is incubated for 15 minutes at 37° C. The particles are then separated and incubated for 15 minutes in the ECL diluent described above.

Labeled Antibodies

To label antibodies with $Ru(bpy)_3^{2+}$ 1 mg of antibody and 0.5 mL of the phosphate-buffered saline (pH 7.8) with 3 mL of 5.0 g/L $Ru(bpy)_3^{2+}$-NHS ester anhydrous dimethyl sulfoxide are mixed. Labeling is allowed to proceed for 30 minutes and then terminated by the addition of 25 μl of 1.0 m/l glycine reagent and further incubated for 10 minutes. The labeled protein is then purified by passage through a Sephadex G25 column, eluted with phosphate buffered saline (pH 7.2) containing a sodium azide, 0.5 g/L. The $Ru(bpy)_3^{2+}$ labeled protein fractions are collected and pooled.

The immunoassays can be performed by mixing 100 mL of sample, 75 mL of coated microparticles and 75 mL of labeled antibody and incubating the mixture with agitation for 15 minutes.

ECL Measurement Cycle

The ECL measurement cycle consists of three steps: 1) preconditioning; 2) measuring; and 3) cleaning. The preconditioning step involves the application of a voltage triangle wave form of 0.0–2.2 volts to −1.0 to +0.6 volts at 2.0 v/sec. The measurement step involves the application of a triangle wave form of +0.6 volts to +2.8 volts to +2.0 volts at 1.0 volts per second. The cleaning step involves the application of a voltage square wave from 0.0 to 3.0 volts to −0.5 to 0.0 volts. All voltages are relative to the Ag/AgCl reference electrode.

EXAMPLE 1

BMG 280 HBsAG Assay Using Flash Buffer

Manual BMG 280 HBsAg assays are carried out (15 min. incubation at 37° C.) and run on ECL detection devices as described above, one having a sandwich magnet configuration of the present invention and the other having a standard capture magnet. The sample compositions are analyzed with both devices at various capture speeds to determine the optimal capture speed. All assays are run using BMG buffers, the RACEF sequence (scan rate 4800 mV/sec and scan limit of 2600 mV) and with the heaters set to 35° C. Exemplary results are shown in Table 1 below.

TABLE 1

BMG 280 HBsAg ASSAYS:
Standard Magnet Vs. Sandwich Magnet on a .012 Cell Gap

| Conc. HBsAg IU/mi | Standard Magnet 25 RPM Capture .012 Cell Gap PMT = 850 V | Standard Magnet 40 RPM Capture .012 Cell Gap PMT = 850 V | Standard Magnet 50 RPM Capture .012 Cell Gap PMT = 850 V | Standard Magnet 60 RPM Capture .012 Cell Gap PMT = 850 V | Sandwich Magnet 40 RPM Capture .012 Cell Gap PMT = 800 V | Sandwich Magnet 50 RPM Capture .012 Cell Gap PMT = 800 V | Sandwich Magnet 60 RPM Capture .012 Cell Gap PMT = 800 V | Sandwich Magnet 70 RPM Capture .012 Cell Gap PMT = 800 V |
|---|---|---|---|---|---|---|---|---|
| (A) 0.0 | 18355.0 | 18873.3 | 21101.0 | 18750.3 | 18878.5 | 17529.0 | 19003.0 | 20020.0 |
| (B) 0.4 | 104129.0 | 103825.5 | 105629.0 | 93109.5 | 112257.0 | 110022.0 | 116978.0 | 109110.0 |
| (C) 0.9 | 191064.0 | 193717.0 | 186641.0 | 170207.5 | 206496.0 | 208652.0 | 213742.0 | 192511.0 |
| (D) 1.7 | 387641.0 | 385489.5 | 385947.0 | 373196.0 | 439848.0 | 431388.0 | 447757.0 | 427354.0 |
| (E) 3.4 | 739747.0 | 731079.5 | 715256.0 | 654474.5 | 841863.0 | 867397.0 | 861976.0 | 791037.0 |
| (H) 30.5 | 6594562.0 | 657824.5 | 6561099.0 | 6295341.8 | 7651280.5 | 7620072.0 | 7630307.3 | 7230209.0 |
| Ratios | | | | | | | | |
| 0.45/0.00 | 5.7 | 5.6 | 5.0 | 5.0 | 5.9 | 6.3 | 6.3 | 5.5 |
| 0.90/0.00 | 10.4 | 10.4 | 8.8 | 9.1 | 11.0 | 11.9 | 11.2 | 9.6 |
| 1.70/0.00 | 21.1 | 20.6 | 18.3 | 19.9 | 23.3 | 24.6 | 23.6 | 21.3 |
| 3.40/0.00 | 40.3 | 39.2 | 33.9 | 34.9 | 44.6 | 49.5 | 45.4 | 39.5 |
| 30.50/0.00 | 359.3 | 351.2 | 310.9 | 335.7 | 405.3 | 434.7 | 401.5 | 361.1 |
| (A) 0.0 - C.V. % | 5.0 | 4.6 | 5.8 | 5.9 | 5.6 | 5.8 | 4.6 | 7.2 |
| (H) 30.5 - C.V. % | 4.3 | 3.1 | 1.4 | 3.4 | 1.7 | 2.0 | 2.3 | 1.9 |
| 2nd Tube Peak Pot. | 2047 | 2047 | 2073 | 2055 | 2179 | 2179 | 2162 | 2215 |
| First AB Reading | 62055 | 62759 | 62968 | 62384 | 46511 | 46787 | 45035 | 46375 |

* The (A) calibrator in standard magnet 50 RPM capture counts are unusually high relative to the other standard magnet runs, thus ratios may show to be falsely low The data in Table 1 shows that, for the standard magnet at a 12 mil cell gap, the optimal capture speed is between about 40 and about 50 RPM. The sandwich magnet, at a 12 mil cell gap, has an optimal capture speed of about 60 RPM. The assay ratios show an increase of approximately 14% when using the sandwich magnet. Using the sandwich magnet for the HBsAg assay, the PMT voltage has to be reduced from 850 V (used with the standard magnet) to 800 V due to the increase of assay counts above the 9.5 million limit. The 50 V change from 800 V to 850 V is believed to cause the ECL counts to increase by a factor of 1.79.

The assay results show a 2.08 fold increase in the counts from the standard to the sandwich magnet. Approximately 50% of the increase is due to the improvement in PMT gain (reduced interference effects on the PMT). The remaining increase is believed to be due to more efficient capture of the beads and/or to the beads lying down in a more optimal configuration which allows for more efficient ECL. Peak potential increases by more than 100 mV with the change of magnets from the standard to the sandwich configuration. This shows how the orientation of the beads on the electrode surface changes with magnet design.

EXAMPLE 2
BMG Non-separation TSH Assay Using Igen Buffer

To further evaluate the performance of the sandwich magnet design, BMG non-separation, thyroid stimulating hormone (TSH) assays are done with the capture pump speed at 40 rpm and 80 rpm. A Lexan 280 cell (cell gap=10 mil) and the RACE280 NEW sequence are used in an Origen 1.5 analyzer as described above with a standard magnet and a four-magnet sandwich magnet. The ECL is measured for TSH calibrators. The capture time for the 40 rpm capture is equal to 16.8 seconds and for the 80 rpm capture it is 8.4 seconds.

Figure 10:
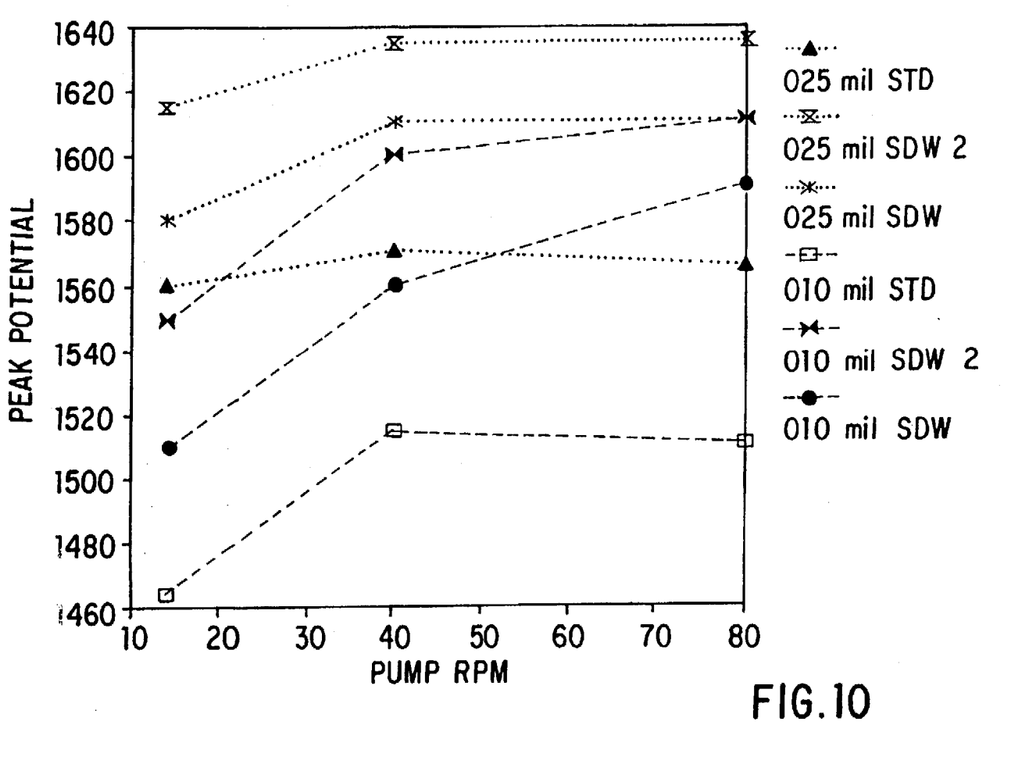
FIG. 10 is a graphic representation of the peak potential (averages) measured by an ECL detection apparatus as a function of pump speed (sample time), with magnets of various configurations.

The results indicate that the sandwich magnet ratios are better than the standard magnet ratios at both 40 rpm and 80 rpm. See FIG. 10. Differences between the magnets in the way they influence bead distribution on the electrode surface is shown again. The peak potentials shift more positive using the sandwich magnet indicating a different bead distribution.

EXAMPLE 3
DNA Probe Assay Using IGEN Buffer

Figure 11:
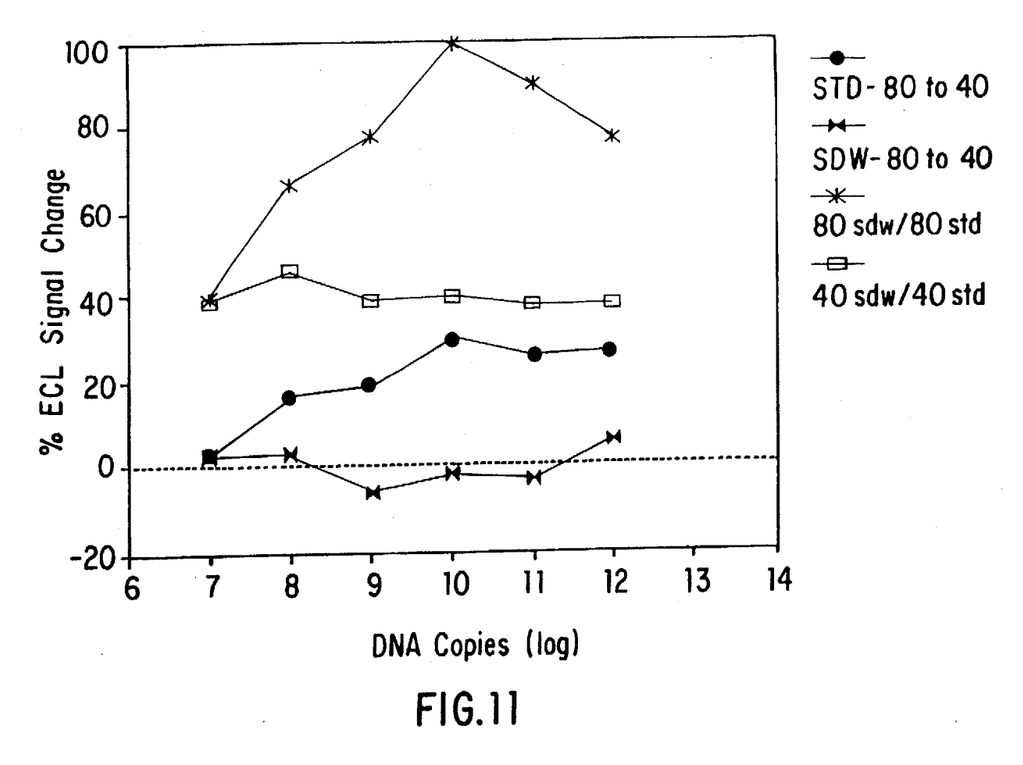
FIG. 11 is a graphic representation of the change in the ECL signal measured by an ECL detection apparatus as a function of pump speed and magnet configuration.

DNA assays are run using the ECL detection devices described above with the standard magnet and the two magnet sandwich configuration at 40 rpm and 80 rpm capture speeds. The ratios do not improve dramatically when using the sandwich magnet; however, the increase in signal magnitudes ranged from 40% to 100% (see FIG. 11). The results also show that by using the sandwich magnet design, the capture rpm can be increased to 80 rpm, allowing a reduction in assay time.

Another observation of these DNA assays is that with the increase in signal from the sandwich design, maintaining the same signal magnitude as with the standard magnet allows an even faster capture speed (capture time decreases by a factor of four). The use of a 40–60 rpm capture speed with the sandwich magnet will provide benefits from both a 40–50% increase in signal and a faster cycle time.

Included within the methods provided by this invention are methods for performing assays such as immunoassays and DNA probe assays in a wide variety of formats. In performing an assay, the labeled complex bound to the microparticle which is detected and quantified is typically formed by a reaction within the solution or participates in a reaction within the solution. The labeled compound can be the analyte of interest, an analog or a component which competes with the analyte of interest. Such compounds are often referred to as "assay producing compounds". Reactions which provide an ECL labeled complex bound to microparticles are well known and some are described in WO92/14138, including:

Example 5—Ru(bpy)$_3^{2+}$ Labeled mouse Igb;

Examples 9 and 10—Ru(bpy)$_3^{2+}$ Labeled mouse anti-TSH; and

Examples 16–18—Preparation of Nucleic Acid Magnetic Particles,

Preparation of Streptavidin Magnetic Particles.

The DNA probe assays of this invention can include polymerization chain reaction (PCR) methods or other amplification methods to increase sensitivity. Suitable sample preparations and testing methods are described in *Clinical Chemistry*, Volume 37, No. 8 (1991), and *Clinical Chemistry*, Volume 38, No. 6 (1992).

The assay methods of the present invention include competitive solid phase sandwich immunoassays where two antibodies specific for different epitopes of the analyte can be used. Specific assay techniques are described more particularly in the following examples of WO/92/14138.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

What is claimed is:

1. An apparatus for the measurement of electrochemiluminescence from a sample composition which comprises:
   a. a cell having a volume which defines the sample composition, an inlet, an outlet, an electrode adapted to apply a voltage to the sample composition and a capture magnet comprising two or more magnetic filed sources adapted to attract and distribute on the electrode surface, magnetically responsive microparticles within the sample composition having an electrochemiluminescent active moiety linked thereto;
   b. means to impress a voltage upon said electrode sufficient to generate luminescence from electrochemiluminescent active moieties bound to the microparticles positioned on the electrode surface; and
   c. means to measure the luminescence generated within the sample composition;

wherein the capture magnet is positioned adjacent said electrode and is selected from the group consisting of one or more sandwich magnets and one or more channel magnets.

2. An apparatus as in claim 1 wherein the capture magnet comprises 2–8 magnetic field sources separated by magnetically responsive material.

3. An apparatus as in claim 1 wherein the capture magnet is adapted to attract and distribute on the electrode surface, magnetically responsive microparticles which have a ruthenium or osmium based electrochemiluminescent active moiety.

4. An apparatus as in claim 1 wherein the capture magnet is a channel magnet and additionally comprises at least one magnetically responsive material positioned to extend a magnetic pole of the single magnetic field source.

5. An apparatus as in claim 1 wherein the magnetically responsive material within the capture magnet has a shape which increases the surface area of the extended magnetic pole of the magnetic field source.

6. An apparatus as in claim 1 wherein the capture magnet is a channel magnet and is adapted to attract and distribute on the electrode surface, magnetically responsive microparticles which have a ruthenium or osmium based electrochemiluminescent active moiety.

7. A method for measuring electrochemiluminescence from a sample composition, wherein said sample composition contains an electrochemiluminescent (ECL) active species that comprises an ECL-active moiety and a magnetically responsive particle, said method comprising:
   a. introducing a known volume of said sample composition into a cell which contains an electrode;
   b. collecting the ECL active species that comprise an ECL active moiety linked to a magnetically responsive particle on a surface of said electrode by imposition of a magnetic field on said magnetically responsive particles;

c. imposing a voltage on said electrode of sufficient magnitude to induce luminescence from the ECL active species within the sample composition; and d. measuring the luminescence emitted from the sample composition;

wherein the magnetic field imposed on said magnetically responsive particles is provided by a capture magnet positioned adjacent the electrode surface and wherein said capture magnet is selected from the group consisting of one or more channel magnets and one or more sandwich magnets.

8. A method as in claim 7, comprising the additional step of separating the ECL active species that comprise an ECL active moiety linked to a magnetically responsive particle from the other components of the sample composition.

9. A method as in claim 8 wherein the additional separating step is performed prior to the step of measuring luminescence from the sample composition.

10. A method as in claim 8, wherein the additional step of separating the ECL-active species captured on the electrode surface from other components is performed after the step of collecting the ECL active species on a surface of said electrode.

11. A method as in claim 7, wherein the magnetically responsive microparticles have a diameter within the range of 0.0001 to 200 microns and a density of from 1.0 to 5.0 g/ml.

12. A method as in claim 7, wherein the step of collecting the ECL active species comprises extending the magnet into the cell and retracting the magnet from the cell prior to the step of imposing a voltage on said electrode.

13. A method as in claim 7 wherein the sample composition is a fluid in motion.

14. A method as in claim 7, where the ECL-active species comprises an ECL active moiety based on ruthenium or osmium.

15. A method as in claim 14, wherein ECL-active species are bound to a cell, subcellular particle, microbe, virus, hapten, antigen, antibody, nucleic acid, or protein.

16. A method as in claim 7, wherein the ECL-active species comprised of an ECL-active moiety linked to a magnetically responsive particle is present in a concentration of less than $10^{-3}$ molar.

17. A method as in claim 7, wherein the ECL-active species comprised of an ECL-active moiety linked to a magnetically responsive particle is present in a concentration of about than $10^{-12}$ molar.

18. A method as in claim 7, wherein the luminescence measured from the sample composition is at least twice that measured from the sample composition wherein the capture magnet does not have a magnetic field source with magnetic flux lines which are dispersed or compressed.

19. An apparatus for the measurement of the electrochemiluminescence from a sample composition which comprises:

a. a cell having a volume which defines the sample composition, an electrode adapted to apply a voltage to the sample composition and a capture magnet comprising one or more magnetic field sources adapted to attract magnetically responsive components within the sample composition to the electrode surface;

b. means to impress a voltage upon said electrode sufficient to generate luminescence from electrochemiluminescent active species within the sample composition; and c. means to measure the luminescence generated within the sample composition;

wherein the capture magnet is selected from the group consisting of one or more sandwich magnets and one or more channel magnets.

20. An apparatus as in claim 19 wherein the magnetic field sources comprise permanent magnets.

21. An apparatus as in claim 19 wherein the capture magnet additionally comprises a magnetically responsive material.

22. An apparatus as in claim 19 wherein the capture magnet is adapted to attract and distribute on the electrode surface, magnetically responsive microparticles which have an electrochemiluminescent moiety linked thereto.

23. An apparatus as in claim 19 wherein the capture magnet is adapted to attract and distribute on the electrode surface, magnetically responsive microparticles which have a ruthenium or osmium based electrochemiluminescent active moiety.

* * * * *